(12) United States Patent
Stewart et al.

(10) Patent No.: US 10,828,425 B2
(45) Date of Patent: Nov. 10, 2020

(54) NEEDLE SHIELD REMOVER AND A MEDICAMENT DELIVERY DEVICE COMPRISING THE NEEDLE SHIELD REMOVER

(71) Applicant: SHL MEDICAL AG, Zug (CH)

(72) Inventors: Justin Stewart, Deerfield Beach, FL (US); Gunnar Elmén, Huddinge (SE); Emil Björk, Stockholm (SE)

(73) Assignee: SHL MEDICAL AG, Zug (CH)

( * ) Notice: Subject to any disclaimer, the term of this patent is extended or adjusted under 35 U.S.C. 154(b) by 279 days.

(21) Appl. No.: 15/631,319

(22) Filed: Jun. 23, 2017

(65) Prior Publication Data

US 2018/0369495 A1    Dec. 27, 2018

(51) Int. Cl.
*A61M 5/32* (2006.01)
*A61M 5/31* (2006.01)

(52) U.S. Cl.
CPC ........ *A61M 5/3202* (2013.01); *A61M 5/3137* (2013.01); *A61M 5/3204* (2013.01); *A61M 2005/3254* (2013.01); *F04C 2270/0421* (2013.01)

(58) Field of Classification Search
CPC .... A61M 5/32; A61M 5/3202; A61M 5/3204; A61M 5/3137; A61M 5/3243; A61M 2005/3254; F16L 25/0063; F16L 25/0091; F16L 37/091; F04C 2270/0421
See application file for complete search history.

(56) References Cited

U.S. PATENT DOCUMENTS

| | | | | |
|---|---|---|---|---|
| 2,888,924 A * | 6/1959 | Dunmire | ............... | A61M 5/282 604/196 |
| 4,373,526 A * | 2/1983 | Kling | .................... | A61M 5/422 604/117 |
| 4,636,201 A * | 1/1987 | Ambrose | ............ | A61M 5/3202 604/192 |
| 4,897,083 A * | 1/1990 | Martell | ............... | A61M 5/3202 604/192 |
| 4,915,697 A * | 4/1990 | DuPont | ................. | A61M 5/326 604/192 |
| 4,931,048 A * | 6/1990 | Lopez | ................. | A61M 5/3202 604/110 |

(Continued)

FOREIGN PATENT DOCUMENTS

| | | | | |
|---|---|---|---|---|
| EP | 2438939 A1 * | 4/2012 | ........ | A61M 5/31513 |
| EP | 2878321 A1 | 6/2015 | | |

(Continued)

OTHER PUBLICATIONS

International Search Report Issued in International Application No. PCT/EP2018/065366 dated Aug. 13, 2018.

*Primary Examiner* — Nathan R Price
*Assistant Examiner* — Mark A Igel
(74) *Attorney, Agent, or Firm* — McDonnell Boehnen Hulbert & Berghoff LLP

(57) ABSTRACT

A needle shield remover for assembly with a cap of a medicament delivery device, wherein the needle shield remover comprises a longitudinally elongated tubular body (10, 10', 10") having a plurality of structural features, wherein said plurality of structural features are symmetrically disposed on the tubular body (10, 10', 10"), in relation to a plane of symmetry which is perpendicular to a longitudinal axis.

8 Claims, 5 Drawing Sheets

(56) References Cited

U.S. PATENT DOCUMENTS

| | | | | |
|---|---|---|---|---|
| 5,098,400 | A * | 3/1992 | Crouse | A61M 5/3204 604/192 |
| 5,147,325 | A * | 9/1992 | Mitchell | A61M 5/3213 604/192 |
| 6,663,145 | B1 * | 12/2003 | Lyall, III | F16L 37/091 285/104 |
| D629,510 | S * | 12/2010 | Grunhut | D24/127 |
| D733,869 | S * | 7/2015 | Ratjen | D24/113 |
| 9,233,212 | B2 * | 1/2016 | Holmqvist | A61M 5/3202 |
| 10,220,157 | B2 * | 3/2019 | Nguyen | A61M 5/31511 |
| 10,300,214 | B2 * | 5/2019 | Maxfield | A61J 1/1412 |
| 2002/0135184 | A1 * | 9/2002 | Snyder, Sr. | F16L 37/091 285/340 |
| 2004/0032125 | A1 * | 2/2004 | Rehder | F16L 37/53 285/307 |
| 2004/0183302 | A1 * | 9/2004 | Allen | F16L 47/32 285/322 |
| 2007/0129686 | A1 * | 6/2007 | Daily | A61M 5/2033 604/192 |
| 2009/0014462 | A1 * | 1/2009 | Costa | A61M 5/3205 221/185 |
| 2012/0238961 | A1 * | 9/2012 | Julian | A61M 5/32 604/192 |
| 2014/0343503 | A1 * | 11/2014 | Holmqvist | A61M 5/3202 604/192 |
| 2015/0051553 | A1 * | 2/2015 | Bjork | A61M 5/3287 604/198 |
| 2016/0144132 | A1 * | 5/2016 | Scanlon | A61M 5/3204 604/192 |
| 2018/0133407 | A1 * | 5/2018 | Kemp | A61M 5/3204 |
| 2018/0369495 | A1 * | 12/2018 | Stewart | A61M 5/3202 |

FOREIGN PATENT DOCUMENTS

| | | | | |
|---|---|---|---|---|
| WO | WO-03045481 | A1 * | 6/2003 | A61M 5/3272 |
| WO | WO-03051423 | A2 * | 6/2003 | A61M 5/3202 |
| WO | 2013058697 | A1 | 4/2013 | |
| WO | WO-2013058697 | A1 * | 4/2013 | A61M 5/3202 |
| WO | WO-2015078868 | A1 * | 6/2015 | A61M 5/3204 |

* cited by examiner

NEEDLE SHIELD REMOVER AND A MEDICAMENT DELIVERY DEVICE COMPRISING THE NEEDLE SHIELD REMOVER

TECHNICAL FIELD

The present disclosure relates to a needle shield remover and in particular to a symmetric needle shield remover for a cap of a medicament delivery device.

BACKGROUND

Today's medicament delivery devices may be complex and involve many different components. Assembly of such devices is time consuming and is often performed manually by trained personnel. The various components are picked from trays and assembled together by orienting the components in relation to each other, and fitting them together. Often different members of one component need to be matched to guides and/or attachments means of one or more other components, sometimes while the components are under bias of a spring. Depending on the complexity of the device, the assembly steps may be numerous. It would therefore be advantageous if the assembly process could be simplified, such as by improving the design of certain components to aid in their assembly.

The present disclosure relates to a needle shield remover. The needle shield remover is often assembled with a cap, or closure member, of a medicament delivery device and is engaged to a needle shield, which protects a needle by hermetically enclosing it. The shield may comprise a flexible rubber member in which the needle is embedded, i.e. a flexible needle shield (FNS). For some applications, the FNS is provided with a rigid outer shell, i.e. a rigid needle shield (FNS). To be able to remove the needle shield before use of the medicament delivery device, the needle shield remover is provided with gripping members that engage the needle shield. Since the needle shield remover is attached to the cap, removal of the cap will also pull away the needle shield from the needle, due to the gripping members' engagement with the needle shield.

An example of a needle shield remover is disclosed in WO2013/058697, wherein a remover body is provided with two different sets of gripping members at a distal part of the remover body. One set of gripping members is configured to be able to engage a FNS and the other set of gripping members is configured to be able to engage a RNS. Both sets of gripping members are arranged on distal part of the remover body. A circumferentially extending ledge or protrusion is provided on a proximal end of the remover body to cooperate with a circumferential groove of a lid piece of a cap, such that the remover body may be assembled with the cap. However, the assembly operation requires the operator to determine which end of the remover body that is to be connected to the lid piece of the cap. The operation is especially time consuming if the needle shield removers are picked from a bulk transport box, instead of a tray containing pre-oriented components.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction of the longest extension of the device or the component.

The term "lateral", with or without "axis", refers to a direction or an axis through the device or components thereof in the direction of the broadest extension of the device or the component. "Lateral" may also refer to a position to the side of a "longitudinally" elongated body.

In a similar manner, the terms "radial" or "transversal", with or without "axis", refers to a direction or an axis through the device or components thereof in a direction generally perpendicular to the longitudinal direction, e.g. "radially outward" would refer to a direction pointing away from the longitudinal axis.

Also, if nothing else is stated, in the following description wherein the mechanical structure of the device and the mechanical interconnection of its components is described, the device is in an initial non-activated or non-operated state.

In view of the foregoing, a general object of the present disclosure is to provide a needle shield remover for a cap of a medicament delivery device, which needle shield remover is easier to assemble.

According to a main aspect of the disclosure it is characterised by a needle shield remover for assembly with a cap of a medicament delivery device, wherein the needle shield remover comprises a longitudinally elongated tubular body having a plurality of structural features, wherein said plurality of structural features are symmetrically disposed on the tubular body, in relation to a plane of symmetry which is perpendicular to a longitudinal axis.

The structural features, such as gripping members and cap fastening members, are symmetrically arranged such that the assembly of the needle shield remover with a the cap can be performed without first orienting the needle shield in a particular longitudinal direction.

According to another object of the present disclosure the plane of symmetry is located at mid-length of the tubular body.

Conceivably, the plane of symmetry could be offset from the longitudinal centre of the tubular body for certain structural features. However, for the assembly of the cap and the needle shield to achieve full independence of longitudinal direction of the needle shield, the plane of symmetry should preferably be located at mid-length of the tubular body.

According to another object of the present disclosure the plurality of structural features comprises a first cap fastening member and a second cap fastening member symmetrically disposed, in relation to the plane of symmetry, at a proximal part of the tubular member and at a distal part of the tubular member, respectively.

As such, the proximal cap fastening member may be used for attachment of the needle shield remover to a cap, if it is oriented towards the cap when picked from a tray, or box, of components. Similarly, the distal cap fastening member may be used for attachment of the needle shield remover to a cap if it is oriented towards the cap when picked from a tray, or box, of components.

According to another object of the present disclosure the plurality of structural features comprises first shield gripping members and second shield gripping members symmetrically disposed on the tubular body proximally of the plane of symmetry and distally of the plane of symmetry, respectively.

According to another object of the present disclosure the plurality of structural features comprises a first combined fastening/gripping member and second combined fastening/gripping member symmetrically disposed, in relation to the plane of symmetry, at a proximal part of the tubular member and at a distal part of the tubular member, respectively, such that a combined fastening/gripping member may be used to attach the needle shield remover to a cap of a medicament delivery device.

According to another object of the present disclosure the plurality of structural features further comprises a third shield gripping member and a fourth shield gripping member symmetrically disposed on the tubular body, closer to the plane of symmetry than the first shield gripping member and the second shield gripping member, respectively.

According to another object of the present disclosure the first, second, third and fourth shield gripping member are radially inwardly extending members, extending towards the plane of symmetry, and configured to engage a circumferential side surface, or a distal end, of a needle shield of a medicament delivery device.

According to another object of the present disclosure the first combined fastening/gripping member and the second combined fastening/gripping member is a radially inwardly extending member, extending towards the plane of symmetry, and configured to engage an attachment member of cap or a circumferential side surface, or a distal end, of a needle shield of a medicament delivery device.

Another main aspect of the present disclosure is characterised by a medicament delivery device comprising the aforementioned needle shield remover.

DETAILED DESCRIPTION

Figure 1:
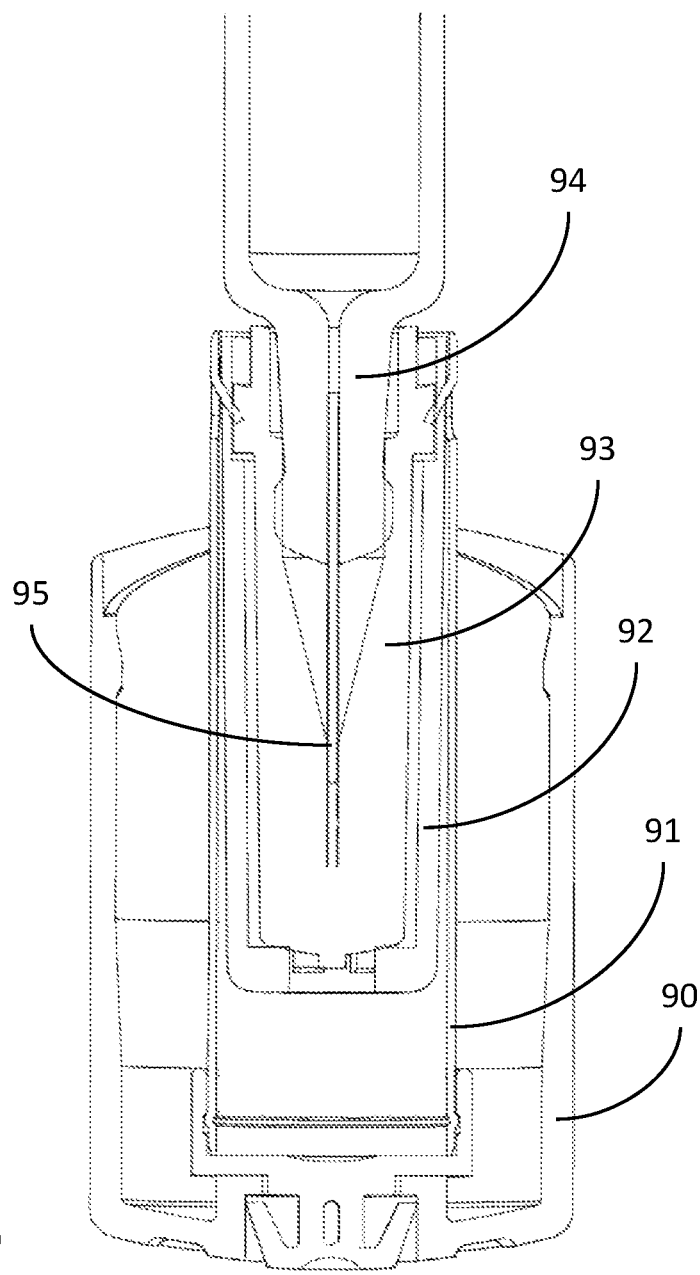
FIG. 1 a cross-sectional view of a prior art cap, needle shield remover, and syringe.

FIG. 1 shows a known needle shield remover 91 comprised in a cap 90. The cap 90 and the needle shield remover 91 are arranged on a rigid needle shield, or RNS 92, which covers a flexible needle shield, or FNS 93. A needle 95, of a syringe 94, is embedded in the FNS 93. The syringe 94 may be housed in a medicament delivery device (not shown), for instance an auto-injector. The needle shield remover 91 is attached to the cap 90 and comprises inwardly-projecting gripping members which engage the RNS 92, either by a distal end thereof or by engagement to a circumferential surface of the RNS, such that removal of the cap pulls the RNS and the FNS away from the needle 95.

The present disclosure relates to a needle shield remover which is intended to be applied to known needle shields, for instance needle shields as shown in FIG. 1. The needle shield remover of the present disclosure is described in detail in conjunction with FIGS. 2-5 below.

Figure 2:
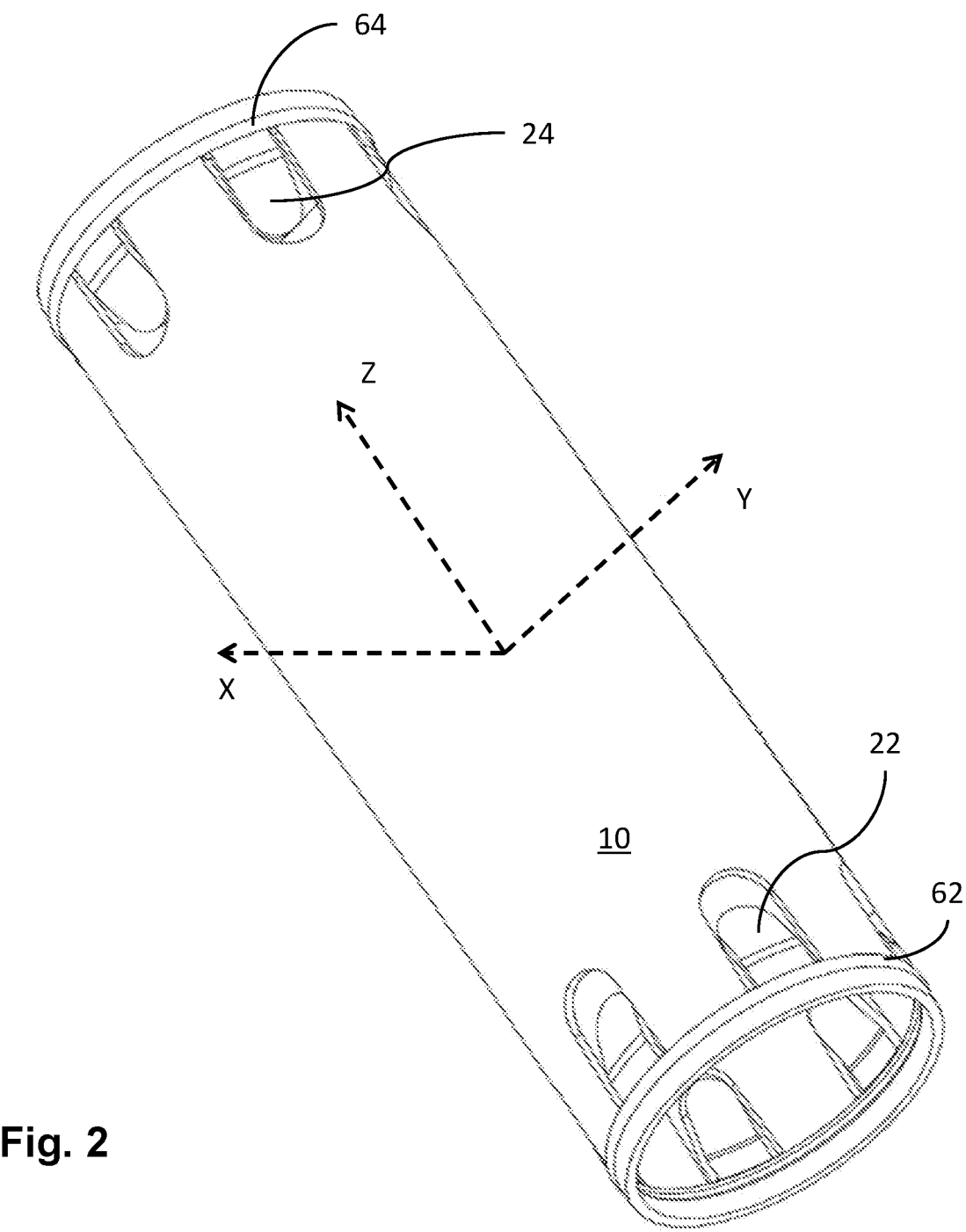
FIG. 2 a perspective view of a needle shield remover according to a first embodiment of the present disclosure.

FIG. 2 shows a needle shield remover according to a first embodiment of the present disclosure. The needle shield remover comprises a longitudinally elongated tubular body 10, elongated along an axis Z. The tubular body has a plurality of structural features. The structural features are symmetrically disposed on the tubular body, in relation to a plane of symmetry which is perpendicular to the longitudinal axis. The plane of symmetry is the X-Y plane, which is perpendicular to the Z axis.

The plane of symmetry is preferably located at mid-length of the tubular body 10. Because the plurality of structural features is disposed symmetrically in relation to the plane located at mid-length if the tubular body 10, it is possible to longitudinally orient the tubular body in either direction when assembling the needle shield remover with a second component, such as with a cap of a medicament delivery device.

The plurality of structural features may comprise a first cap fastening member 62 and a second cap fastening member 64 symmetrically disposed, in relation to the plane of symmetry, at a proximal part of the tubular member and at a distal part of the tubular member 10, respectively. The first and second cap fastening members are identical to each other, but mirrored in the plane of symmetry.

In the embodiment shown in FIG. 2, the first cap fastening member 62 and the second cap fastening member 64 may be configured as circumferentially extending annular protrusions in order to engage a corresponding structure of a cap with which the needle shield remover 10 is going to be assembled. However, the cap fastening members could have many other shapes, as deemed suitable by a skilled person, as long as the connection is made strong enough to withstand the longitudinal force required to remove a needle shield from a needle. Examples of other cap fastening member configurations are snap-fits, ledges, hooks, bumps, grooves, etc.

The plurality of structural features may comprise first shield gripping members 22 and second shield gripping members 24 symmetrically disposed, in relation to the plane of symmetry, at a proximal part of the tubular member and at a distal part of the tubular member 10, respectively. The first and second cap fastening members are identical to each other, but mirrored in the plane of symmetry.

The first shield gripping member 22 and the second shield gripping member 24 may be configured as cut-outs, or tongues, formed out of a circumferential wall of the tubular body 10. They are resilient, radially inwardly extending members, extending towards the plane of symmetry, and configured to engage a distal end, or a circumferential side surface, of a needle shield of a medicament delivery device. The structure of individual gripping members is conventional with regard to the state of the art.

When the medicament delivery device is assembled, the needle shield remover is first attached to a cap by means of the proximal (e.g. first) cap fastening member. In accordance with the present disclosure, and thanks to the symmetrical configuration of the needle shield remover, the tubular body 10 of the needle shield remover may be rotated in either longitudinal direction towards the cap, making the assembly step simple and quick. The cap comprising the needle shield remover is intended to be mounted over the proximal end of a medicament delivery device, to protect a delivery member, e.g. an injection needle.

Secondly, the cap, comprising the needle shield remover 10, is mounted on the medicament delivery device having the injection needle and the needle shield, such that the tubular body 10 of the needle shield remover slides axially along the needle shield until the distal (e.g. second) shield gripping member 24 engages an engagement member on the circumferential side surface of the needle shield, or passes the distal end of the needle shield. The needle shield is somewhat conical, having a distal end which is wider that a proximal end, such that the distal shield gripping member is pushed radially outwards as the tubular body 10 moves distally in relation to the needle shield. When the shield gripping member passes the distal end of the needle shield, the distal shield gripping member relaxes radially inwards and snaps in behind the needle shield remover. Since the distal shield gripping member extends toward the plane of symmetry, it extends proximally, towards a distally-facing end surface of the needle shield. The distally-facing end surface of the needle shield is thereby engaged by the distal shield gripping member.

If a user subsequently removes the cap 50 from the medicament delivery device, the engagement of the proximal cap fastening member to the cap, and the engagement of the distal shield gripping member to the needle shield, will remove the needle shield from the injection needle, and consequently from the medicament delivery device, making the injection needle ready for use.

Figure 3:
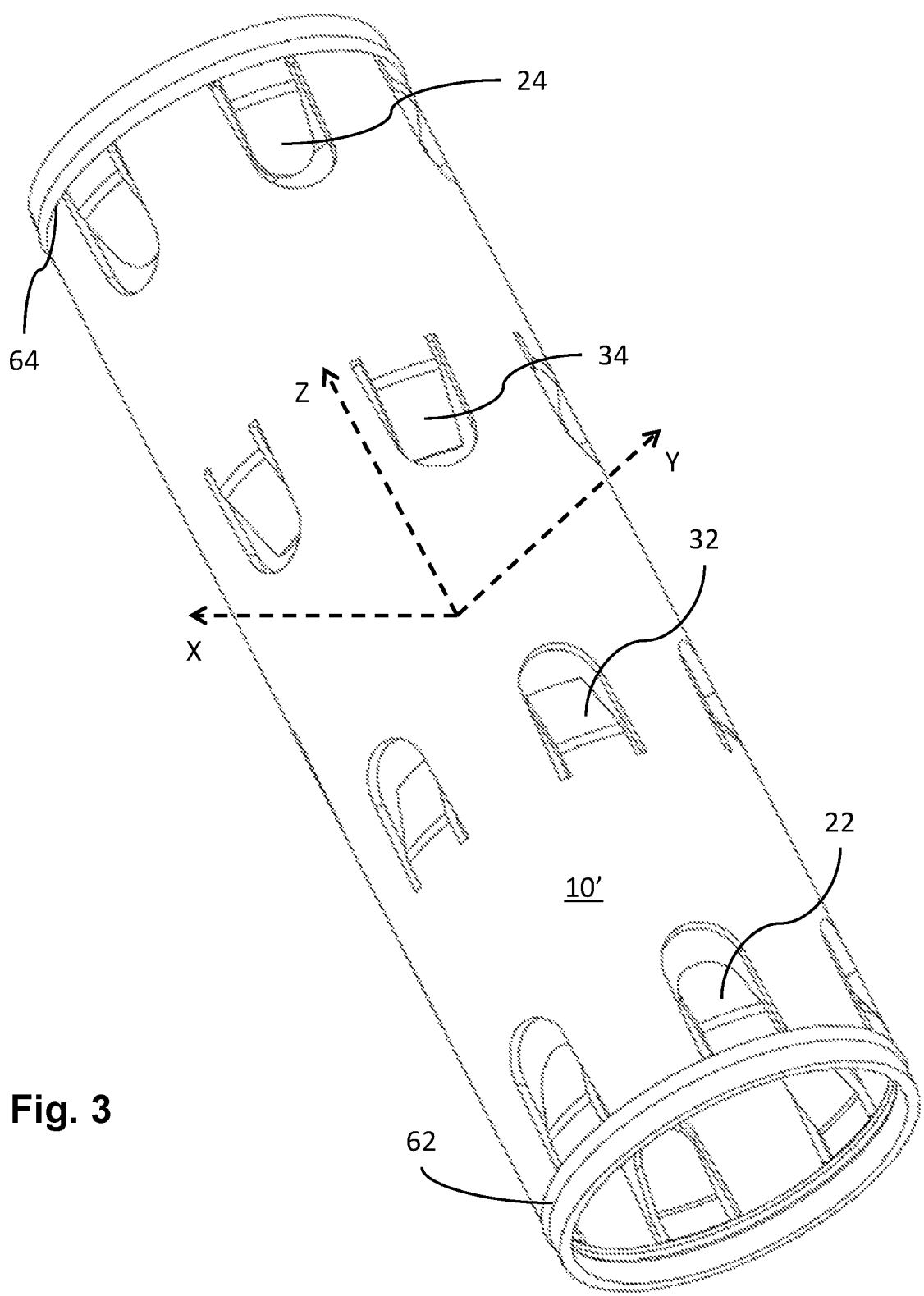
FIG. 3 a perspective view of a needle shield remover according to a second embodiment of the present disclosure.

In an second alternative embodiment, shown in FIG. 3, the plurality of structural features further comprises a third shield gripping member 32 and a fourth shield gripping member 34 symmetrically disposed on the tubular body 10', closer to the plane of symmetry than the first shield gripping member 22 and the second shield gripping member 24, respectively. As such, the third shield gripping member 32 and the fourth shield gripping member 34 may be used to either provide an additional grip on a needle shield, i.e. in addition to the first shield gripping member 22 or to the second shield gripping member 24, respectively, or to engage a circumferential side surface or a distal end of a needle shield which is too short to be properly engaged by the more distal shield gripping member.

The assembly steps of this second alternative embodiment are similar to the assembly steps described above.

Figure 4:
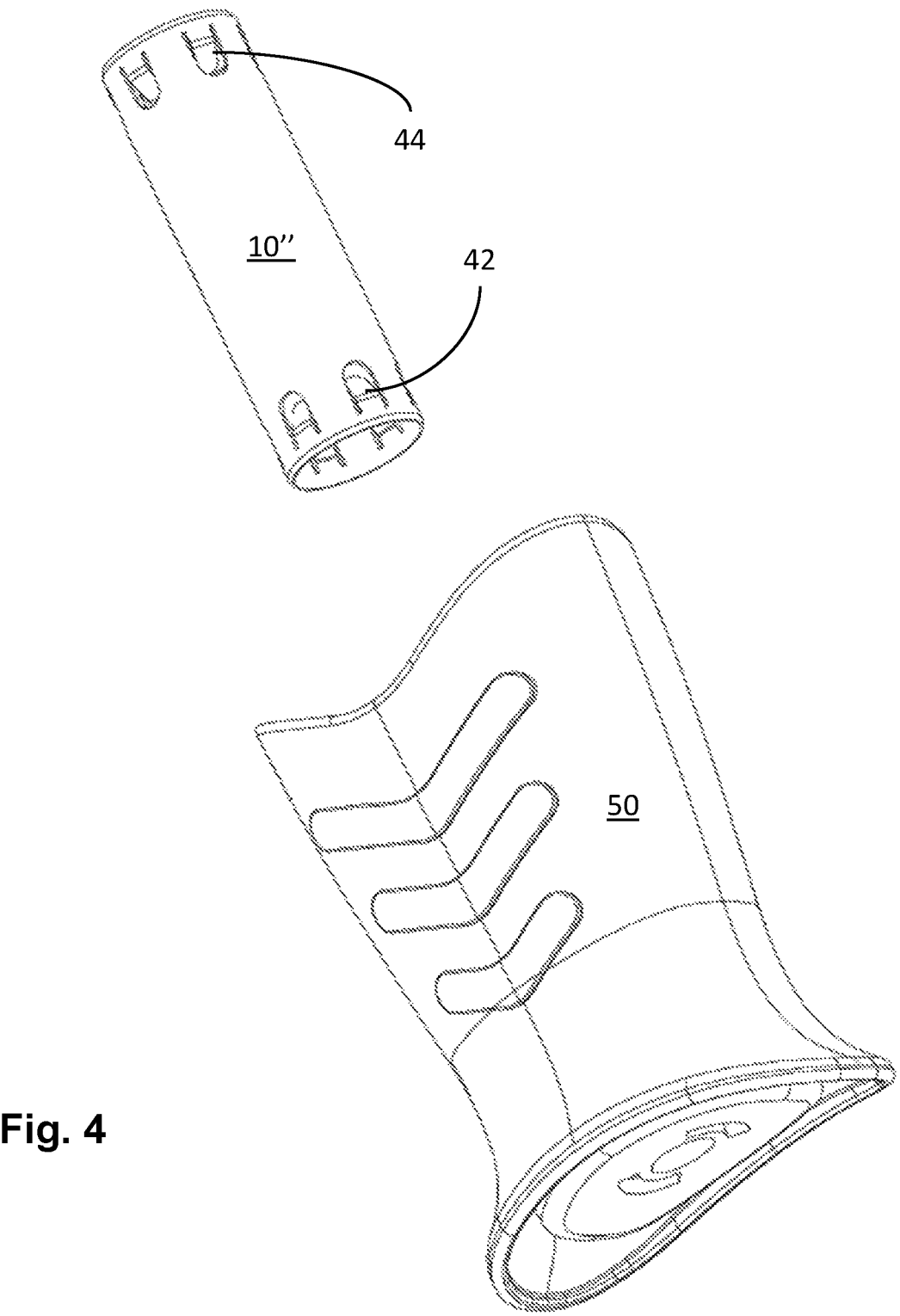
FIG. 4 an exploded perspective view of a cap and a needle shield remover according to a third embodiment of the present disclosure.
Figure 5:
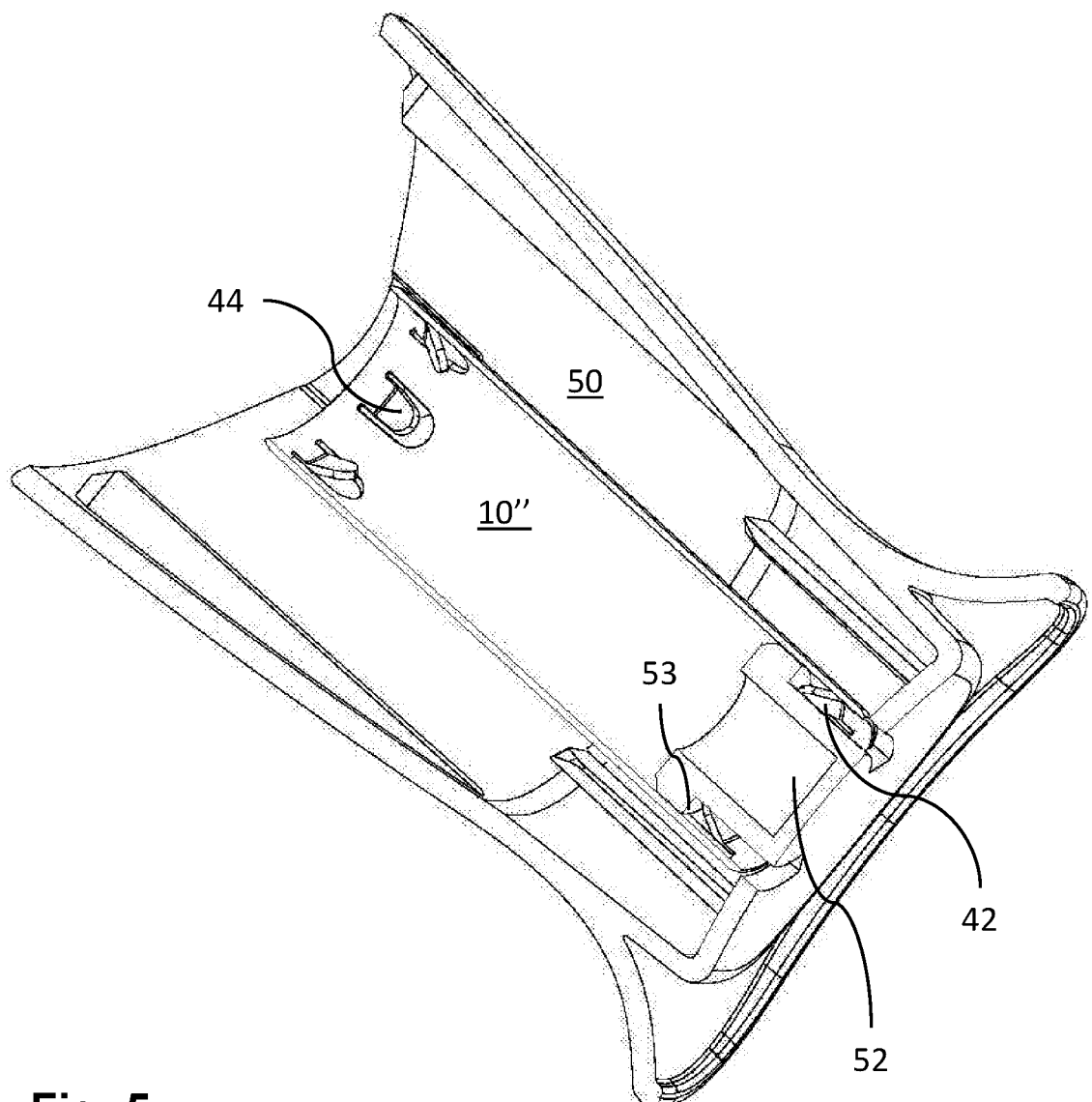
FIG. 5 a cross-sectional view of a cap and a needle shield remover according to a third embodiment of the present disclosure.

In a third alternative embodiment, shown in FIGS. 4 and 5, the plurality of structural features comprises a first combined fastening/gripping member 42 and a second combined fastening/gripping member 44 symmetrically disposed, in relation to the plane of symmetry, at a proximal part of the tubular member 10" and at a distal part of the tubular member 10", respectively, such that a combined fastening/gripping member (42, 44) may be used to attach the needle shield remover to a cap of a medicament delivery device.

The first and second combined fastening/gripping members are identical to each other, but mirrored in the plane of symmetry. The first combined fastening/gripping member 42 replaces the first cap fastening member 62 and the first shield gripping member 22 such that the first combined fastening/gripping member 42 may be used either to attach the needle shield remover to an attachment member 52 of a cap 50, or to engage the circumferential side surface or the distal end of a needle shield, depending on the orientation of the tubular body 10" of the needle shield remover. In accordance with the description above, the second combined fastening/gripping member 44 replaces the second cap fastening member 64 and the second shield gripping member 24 such that the second combined fastening/gripping member 44 may be used either to attach the needle shield remover to an attachment member 52 of a cap 50, or to engage the distal end of a needle shield.

Similar to the description above, the combined fastening/gripping members may be configured as cut-outs, or tongues, formed out of a circumferential wall of the tubular body 10". They are resilient, radially inwardly extending members, extending towards the plane of symmetry, and configured to engage a circumferential side surface or a distal end of a needle shield of a medicament delivery device, or an attachment member 52 of a cap 50. The structure of individual combined fastening/gripping members is conventional with regard to the shield gripping members of the state of the art. Hence, structurally, the combined fastening/gripping member is identical to the shield gripping member described above. However, the combined fastening/gripping members may be located closer to the distal and longitudinal ends of the tubular body 10" of the needle shield remover in order to improve the engagement and/or attachment to the attachment member 52 of the cap 50.

The cap 50 comprises an attachment member 52 configured to enable engagement to a proximal combined fastening/gripping member of the needle shield remover, such that the cap 50 and the needle shield remover are rotationally movable, but axially fixed relative to each other.

The attachment member 52 comprises a proximally-facing annular surface 53 with which a combined fastening/gripping member may engage.

The proximally-facing annular surface 53 of the attachment member 52 thereby essentially mimics the end surface of the needle shield in order to enable engagement with a corresponding shield gripping member (i.e. combined fastening/gripping member).

The invention claimed is:

1. A needle shield remover for assembly with a cap of a medicament delivery device, wherein the needle shield remover comprises:
   a longitudinally elongated tubular body;
   a first annular protrusion that extends radially outward from a first end of the longitudinally elongated tubular body, wherein the first annular protrusion is configured for a first snap fit connection with an attachment structure of the cap;
   a second annular protrusion that extends radially outward from a second end of the longitudinally elongated tubular body, wherein the second annular protrusion is configured for a second snap fit connection with the attachment structure, wherein the first annular protrusion and the second annular protrusion are symmetric with respect to a plane of symmetry that is perpendicular to a longitudinal axis of the needle shield remover;
   a first group of gripping members at the first end configured to engage a distal surface of a needle shield when the second annular protrusion has the second snap fit connection with the attachment structure; and
   a second group of gripping members at the second end configured to engage the distal surface of the needle shield when the first annular protrusion has the first snap fit connection with the attachment structure, wherein the first group of gripping members and the second group of gripping members are symmetric with respect to the plane of symmetry, wherein the plane of symmetry is located at mid-length of the longitudinally elongated tubular body.

2. The needle shield remover according to claim 1, wherein at least one of the first group of gripping members and the second group of gripping members comprises a cut out formed from the longitudinally elongated tubular body.

3. The needle shield remover according to claim 1, wherein each of the first group of gripping members and the second group of gripping members comprises a tongue formed from the longitudinally elongated tubular body.

4. The needle shield remover according to claim 1, wherein each of the first group of gripping members and the second group of gripping members comprises a resilient, radially inwardly extending member.

5. The needle shield remover according to claim 1, wherein the needle shield remover has rotational symmetry about the longitudinal axis.

6. The needle shield remover according to claim 1, wherein each gripping member of the first group of gripping members and the second group of gripping members extends from the longitudinally elongated tubular body radially inward and towards the plane of symmetry and is configured to engage a circumferential side surface, or the second end, of the needle shield of the medicament delivery device.

7. A medicament delivery device comprising the needle shield remover according to claim 1.

8. The needle shield remover according to claim 1, further comprising the cap.

* * * * *